United States Patent [19]

Dean, Jr. et al.

[11] Patent Number: 5,100,783
[45] Date of Patent: * Mar. 31, 1992

[54] WEIGHTED MICROSPONGE FOR IMMOBILIZING BIOACTIVE MATERIAL

[75] Inventors: Robert C. Dean, Jr., Norwich, Vt.; Frederick Cahn, Bellmont, Mass.; Philip G. Phillips, Norwich, Vt.

[73] Assignee: Verax Corporation, Hanover, N.H.

[ * ] Notice: The portion of the term of this patent subsequent to Aug. 29, 2006 has been disclaimed.

[21] Appl. No.: 333,831

[22] Filed: Apr. 5, 1989

Related U.S. Application Data

[63] Continuation of Ser. No. 224,239, Jul. 25, 1988, abandoned, which is a continuation of Ser. No. 732,736, May 10, 1985, abandoned.

[51] Int. Cl.$^5$ .............. C12P 21/00; C12N 11/02; C12N 5/02; C12N 1/20
[52] U.S. Cl. .................. 435/69.1; 435/70.21; 435/70.3; 435/172.1; 435/174; 435/176; 435/177; 435/240.23; 435/240.24; 435/240.26; 435/252.3; 436/548; 530/356; 935/60
[58] Field of Search .............. 435/68, 170, 171, 172.1, 435/174, 177, 178, 179, 180, 240.23, 240.24, 240.26, 252.3; 530/356; 436/548

[56] References Cited

U.S. PATENT DOCUMENTS

| | | | |
|---|---|---|---|
| 3,242,055 | 3/1966 | DeLucia | 195/63 |
| 3,640,829 | 2/1972 | Elton | 161/159 |
| 3,681,093 | 8/1972 | Tsuzuki et al. | 99/175 |
| 3,717,551 | 2/1973 | Bizzini et al. | 435/240 |
| 3,843,446 | 10/1974 | Vieth et al. | 195/68 |
| 3,850,751 | 11/1974 | Messing | 195/63 |
| 3,919,048 | 11/1975 | Dahlmans et al. | 195/63 |
| 3,920,593 | 11/1975 | Adama et al. | 260/2.5 N |
| 3,928,143 | 12/1975 | Coughlin et al. | 195/115 |
| 3,930,951 | 1/1976 | Messing | 195/63 |
| 3,972,776 | 8/1976 | Vieth et al. | 195/65 |
| 3,977,941 | 8/1976 | Vieth et al. | 195/63 |
| 3,978,855 | 9/1976 | McRae et al. | 128/156 |
| 4,009,286 | 2/1977 | Moll et al. | 426/13 |
| 4,012,265 | 3/1977 | Rinde | 106/122 |
| 4,036,693 | 7/1977 | Levine et al. | 195/1.8 |
| 4,041,103 | 8/1977 | Davision et al. | 260/857 D |
| 4,048,018 | 9/1977 | Coughlin et al. | 195/115 |
| 4,060,081 | 11/1977 | Yannas et al. | 128/156 |
| 4,061,466 | 12/1977 | Sjoholm et al. | 23/230 |
| 4,063,017 | 12/1977 | Tsao et al. | 536/57 |
| 4,066,512 | 1/1978 | Lai et al. | 195/127 |
| 4,070,246 | 1/1978 | Kennedy et al. | 195/9 |
| 4,070,300 | 1/1978 | Moroni et al. | 252/190 |
| 4,071,409 | 1/1978 | Messing et al. | 195/63 |
| 4,079,099 | 3/1978 | Gergen et al. | 260/876 B |
| 4,079,100 | 3/1978 | Gergen et al. | 260/876 B |
| 4,080,403 | 3/1978 | Gergen et al. | 260/876 B |

(List continued on next page.)

FOREIGN PATENT DOCUMENTS 1170001 7/1984 Canada.

(List continued on next page.)

OTHER PUBLICATIONS

Silman, et al., Biopolymers, vol. 4, 1966, pp. 441–448.
Chemical Modification of Collagen Fibers with Carbodiimides, Chonan, Yasumasa; Matsunaga, Ayako; Toyoda, Harukazu (Leather Res. Inst., Tokyo Univ. Fuchu, Japan, Hikaku Kagaku 1974, 20(1), 29–26 (Japan).

(List continued on next page.)

Primary Examiner—David M. Naff
Attorney, Agent, or Firm—Banner, Birch, McKie & Beckett

[57] ABSTRACT

Weighted microsponges formed of a porous, biostable matrix of a biocompatible polymer containing an inert weighing material are prepared suitable for use in culturing organisms in motive reactor systems. The matrix has an open to the surface pore structure with an average pore size in the range of from about 1 to about 150 microns and the pores occupy from about 70 to about 98% by volume of the microsponge. The microsponges have an average particle size of from about 100 to about 1000 microns and a specific gravity of above about 1.05. Biocompatible polymers that can be used are polysaccharides, proteins and synthetic polymers and the weighing material can be metals, metal alloys, metal oxides or ceramics.

21 Claims, 2 Drawing Sheets

| Patent # | Date | Inventor | Class |
|---|---|---|---|
| 4,081,424 | 3/1978 | Gergen et al. | 260/42.18 |
| 4,085,163 | 4/1978 | Gergen et al. | 260/857 D |
| 4,085,203 | 4/1978 | Telling et al. | 424/89 |
| 4,088,626 | 5/1978 | Gergen et al. | 260/42.18 |
| 4,088,627 | 5/1978 | Gergen et al. | 260/42.18 |
| 4,088,711 | 5/1978 | Gergen et al. | 260/873 |
| 4,090,022 | 5/1978 | Tsao et al. | 536/57 |
| 4,090,996 | 5/1978 | Gergen et al. | 260/40 R |
| 4,092,219 | 5/1978 | Lin et al. | 195/29 |
| 4,096,204 | 6/1978 | Gergen et al. | 260/876 B |
| 4,101,605 | 7/1978 | Gergen et al. | 260/873 |
| 4,102,746 | 7/1978 | Goldberg | 195/63 |
| 4,102,854 | 7/1978 | Gergen et al. | 260/42.18 |
| 4,107,130 | 8/1978 | Gergen et al. | 260/40 R |
| 4,107,131 | 8/1978 | Gergen et al. | 260/40 TN |
| 4,110,303 | 8/1978 | Gergen et al. | 260/42.18 |
| 4,111,894 | 9/1978 | Gergen et al. | 260/40 R |
| 4,111,895 | 9/1978 | Gergen et al. | 260/42.18 |
| 4,111,896 | 9/1978 | Gergen et al. | 260/42.18 |
| 4,119,607 | 10/1978 | Gergen et al. | 260/40 R |
| 4,126,600 | 11/1978 | Gergen et al. | 260/42.18 |
| 4,127,447 | 11/1978 | Griffith et al. | 195/116 |
| 4,138,290 | 2/1979 | McMullen et al. | 195/31 F |
| 4,138,292 | 2/1979 | Chibata et al. | 195/59 |
| 4,144,126 | 3/1979 | Burbidge | 435/240 |
| 4,149,936 | 4/1979 | Messing et al. | 195/56 |
| 4,153,510 | 5/1979 | Messing et al. | 195/59 |
| 4,169,761 | 10/1979 | Precausta et al. | 435/235 |
| 4,177,253 | 12/1979 | Davies et al. | 424/1 |
| 4,189,534 | 2/1980 | Levine et al. | 435/2 |
| 4,203,801 | 5/1980 | Telling et al. | 435/284 |
| 4,224,413 | 9/1980 | Burbidge | 435/284 |
| 4,238,480 | 12/1980 | Sawyer | 424/177 |
| 4,241,176 | 12/1980 | Avrameas et al. | 435/7 |
| 4,242,470 | 12/1980 | Gergen et al. | 525/92 |
| 4,247,498 | 1/1981 | Castro | 264/41 |
| 4,250,267 | 2/1981 | Hartdegen et al. | 435/317 |
| 4,266,029 | 5/1981 | Branner-Jorgensen | 435/176 |
| 4,266,032 | 5/1981 | Miller et al. | 435/241 |
| 4,280,954 | 7/1981 | Yannas et al. | 260/123.7 |
| 4,286,061 | 8/1981 | Messing et al. | 435/176 |
| 4,287,305 | 9/1981 | Compere et al. | 435/176 |
| 4,293,654 | 10/1981 | Levine et al. | 435/241 |
| 4,303,533 | 12/1981 | Fremont | 210/791 |
| 4,304,857 | 12/1981 | Brouillard et al. | 435/94 |
| 4,305,926 | 12/1981 | Everse et al. | 424/14 |
| 4,312,946 | 1/1982 | Wood et al. | 435/182 |
| 4,321,327 | 3/1982 | Chen et al. | 435/161 |
| 4,323,650 | 4/1982 | Rosevear | 435/174 |
| 4,352,887 | 10/1982 | Reid et al. | 435/109 |
| 4,373,027 | 2/1983 | Berneman et al. | 435/240 |
| 4,374,121 | 2/1983 | Cioca | 424/19 |
| 4,378,017 | 3/1983 | Kosugi et al. | 424/35 |
| 4,384,044 | 5/1983 | Kim et al. | 435/101 |
| 4,385,093 | 5/1983 | Hubis | 428/316.6 |
| 4,386,129 | 5/1983 | Jacoby | |
| 4,388,331 | 6/1983 | Miller | 426/63 |
| 4,409,247 | 10/1983 | Baret et al. | 426/41 |
| 4,412,947 | 11/1983 | Cioca | 530/356 |
| 4,415,668 | 11/1983 | Siegel | 435/241 |
| 4,430,451 | 2/1984 | Young et al. | 521/64 |
| 4,430,760 | 2/1984 | Smestad | 3/1.9 |
| 4,456,685 | 6/1984 | Guthrie | 435/109 |
| 4,479,876 | 10/1984 | Fuchs | 210/605 |
| 4,519,909 | 5/1985 | Castro | 210/500.2 |
| 4,997,753 | 2/1991 | Dean, Jr. et al. | 436/69.1 |

FOREIGN PATENT DOCUMENTS

| | | |
|---|---|---|
| 0053869 | 6/1982 | European Pat. Off. . |
| 97907 | 1/1984 | European Pat. Off. ............ 435/241 |
| 0109124 | 5/1984 | European Pat. Off. . |
| 2912827 | 10/1980 | Fed. Rep. of Germany . |
| WO82/00660 | 3/1982 | PCT Int'l Appl. . |
| 697521 | 7/1977 | U.S.S.R. . |
| 1426101 | 2/1976 | United Kingdom . |
| 2059991 | 4/1981 | United Kingdom . |

OTHER PUBLICATIONS

Intracatenare Vernetzung von Gelatine mit Carbodiimide, Helvetica Chimica Acta–vol. 55, Fasc. 7(1972)–Nr. 247, pp. 2468.

Design of an Artificial Skin. I. Basic Design Priciples, L. V. Yannas and John F. Burke, Journal of Biomedical Materials Research, vol. 14, 65–81 (1980).

Design of an Artifical Skin. II. Control of Chemical Composition, Yannas and Burke, Gordon, Huang, Rubnestein, Journal of Biomedical Materials Research vol. 14, 107–131 (1980).

Leighton, *Journal of the National Cancer Institute*, 12 (1951–52) pp. 545–551.

Jacobson, et al., *Biochimica et Biophysica Acta*, 506 (1978) pp. 81–96.

Kuo et al. (1981) *In Vitro* 17:901–906.

Van Wezel, et al. (1983) *In Vitro*, 19:259.

Feder, et al. (1983) *In Vitro*, 19:260.

Feder and Tolbert (1983), *Scientific American* 248:36–43.

Karkare, et al. (1984) *Continuous Production of Monoclonal Antibodies by Chemostatic and Immobilized Hybridoma Culture* American Chemical Society Annual Meeting, Aug. 27, 1984.

(List continued on next page.)

OTHER PUBLICATIONS

Encyclopedia of Polymer Science and Technology, vol. 1, (1964), pp. 186, 742-747.

Kolot, F. B., "Microbial Carriers-Strategy for Selection", Process Biochemistry, Aug./Sep. 1981.

Vieth et al., "Immobilized Microbial Cells in Complex Biocatalysis", American Chemical Society, 1979.

Venkatasubramanian, "Biocatalysis by Membrane-Attached Enzymes and Whole Microbial Cells", Desalination, vol. 35, 1980, pp. 353-363.

Venkatasubramanian et al., "On the Mechanisms of Enzyme and Whole Microbial Cell Attachment to Collagen", *J. Ferment. Technol.*, vol. 52, No. 4, pp. 268-278 (1974).

Venkatasubramanian et al., "Synthesis of Organic Acids and Modification of Steroids by Immobilized Whole Microbial Cells", *Enzyme Engineering*, vol. 3, (1978), pp. 29-41.

Venkatasubramanian et al., "Immobilized Microbial Cells", *Progress in Industrial Microbiology*, vol. 16, pp. 61-86 (1979).

Lindsey et al., "A Novel Method for the Immobilisation and Culture of Plant Cells", FEBS Letters, vol. 155, No. 1, pp. 143-149 (May 1983).

Chemical Abstracts (81) No. 23770n (1974).

WEIGHTED MICROSPONGE FOR IMMOBILIZING BIOACTIVE MATERIAL

This invention was made in the course of, or under, a contract with NIH. The government has rights to the invention pursuant to Grant No. CA37430.

This application is a continuation of application Ser. No. 224,239, filed July 25, 1988 now abandoned, which is a continuation of application Ser. No. 732,736, filed May 11, 1985, now abandoned.

BACKGROUND OF THE INVENTION

1. Field of the Invention

The present invention pertains to the art of immobilizing bioactive materials and particularly relates to an improved microsponge for use in motive bioreactor systems. The present invention also relates to the art of culturing microorganisms and cells, hereinafter referred to collectively as organisms, and particularly relates to the culturing of organisms immobilized on and/or in microsponges in motive reactor systems as submerged suspensions.

2. Description of the Prior Art

Various arrangements for immobilizing bioactive materials are known. Solid supports have long been used for immobilizing microorganisms in the treatment of waste water and related fermentation processes. More recently, solid microcarriers have been used to obtain high cell densities in the culture of attachment-dependent cells. For example, microporous polymeric supports fabricated for example from dextran have been used for cultivating cells. Such supports can be obtained commercially from Pharmacia Fine Chemicals under the brand name Cytodex®. Such solid bio-supports, however, are not suitable for motive reactor systems such as vigorously stirred tanks and fluidized beds since substantially all of the cells are adherent to the surface of said supports and thus are exposed to impact stress and trauma during operation.

Porous inorganic microcarriers also are known and such supports potentially provide protection for the cells in motive applications since the cells populate the interior of the microcarriers. Unfortunately, inorganic microcarriers cannot be made with the proper combination of permeability and specific gravity to function well in all motive applications. For example, the porous fritted glass or cordierite supports described in Messing et al. U.S. Pat. No. 4,153,510 would typically exhibit specific gravities in aqueous suspension of less than about 1.3 if their void fractions are greater than about 80% (Note that void fractions for the Messing supports are not disclosed). Quite understandably, these supports are not suitable for all motive rector systems where a higher specific gravity generally is needed to ensure high relative velocities for maximum rates of mass transfer. Consequently, these supports have generally been relegated for use in packed bed applications.

An object of the present invention is to provide a microsponge containing immobilized bioactive materials suitable for use in motive reactor systems.

An object of the present invention is to provide a microsponge suitable for immobilizing a large variety of microorganisms characterized by wide variations in size and their degree of attachment to solid supports.

A further object of the present invention is to provide a microsponge suitable for motive reaction systems which permits the continued growth and reproduction of immobilized organisms.

It also is An object of the present invention is to provide a microsponge suitable for motive reactor systems which is conducive to maximizing the metabolic activity of immobilized organisms.

Yet Another object of the present invention is to provide a method for continuously culturing organisms of high concentrations.

Still Another object of the present invention is to provide a microsponge suitable for motive reactor systems which permits the culturing of organisms at high concentrations while accommodating either maximum growth rate or maximum metabolic activity.

These and other objects of this invention will become apparent from a consideration of the specification and appended claims.

SUMMARY OF THE INVENTION

The present invention pertains to a weighted microsponge for immobilizing bioactive materials in motive bioreactor systems, said microsponge comprising a porous, biostable matrix of a biocompatible polymer containing an inert weighting material, said matrix having an open to the surface pore structure with an average pore size in the range of from about 1 micron to about 150 microns, with the pores of said matrix occupying from about 70% to about 98% by volume of the microsponge, said microsponge also having an average particle size of from about 100 microns to about 1000 microns and a specific gravity of above about 1.05.

DETAILED DESCRIPTION

Figure 1:
FIG. 1 is a photomicrograph showing a suitable collagen microsponge matrix of the present invention illustrating a fibrous structure.

The present invention is directed to a weighted microsponge prepared from a biocompatible polymer containing immobilized bioactive materials, particularly organisms, suitable for use in motive bioreactor systems. As used throughout the specification and claims, the term "bioreactive material" broadly encompasses enzymes and other chemical factors such as chelating agents, hormones, antibodies, etc., and organisms, i.e., microorganisms and the cells of higher organisms. The organisms may be either living or dead and may be derived without limitation from such diverse sources as bacteria, viruses, fungi, algae, yeasts, animal cells (tissue), e.g., mammals, insects and fish and plant cells. Since the invention has particular advantages when used for culturing organisms, it generally will be described with reference to such embodiments, although it is not to be so-limited.

The microsponge of this invention is prepared from a biocompatible (e.g., non-toxic) polymer that is stable in service for an appropriate period of time, e.g., on the order of months. Biocompatability refers to the ability of the polymeric (matrix) material to support a viable culture of organisms without substantially adversely affecting any desired characteristic of the immobilized organisms, e.g., in the case of hybridomas, the matrix material should not undesirably reduce the production of monoclonal antibodies. The stability or biostability of the matrix material refers to its ability to maintain its strength and integrity under in vitro conditions over the relevant time period for culturing the organism of interest. For example, in the case of a hybridoma culture for producing monoclonal antibodies, it is expected that the motive bioreactor would be operated continuously for three to six months or more. Thus, the matrix material should be biostable for this time period.

Both natural and synthetic polymeric materials can be used as the matrix material. Examples of suitable polymers include polysaccharides such as dextran, dextrin, starchy, cellulose, agarose, carrageenan and the like; proteins such as collagen and the like; and synthetic polymers such as polyvinyl alcohols, polyacrylates, polymethacrylates, polyacrylamides, polyesters, polyurethanes, polyamides and the like. Generally, a material's biocompatability and biostability can be verified using routine experimentation.

Based on its biocompatability and strength, collagen is presently the material of choice. Collagen is a biodegradable polymer found in animals, including man. It has numerous uses in the medical art and in most applications is reconstituted and crosslinked into an insoluble form using various crosslinking agents, such as aldehydes, e.g., glutaraldehyde and formaldehyde; ethylchloroformate; dimethyl adipimidate; N,N-methylenebisacrylamide; 1,2-diacrylamide ethyleneglycol; cyanamide; N,N'-diallyltartardiamide; cyanogen bromide; concanavalin A; 6-amionohexanoic acid; 1,6-diaminohexane; succinidyl active esters; carbodiimides and compounds having similar crosslinking groups and/or physical treatment techniques such as freeze-drying and severe dehydration at a vacuum of about 50 millitors or more and at a temperature ranging from 50° C. to 200° C. Crosslinked collagen has an improved resistance to degradation by collagenase and other proteinases, and this is suitable as the biocompatible polymer for the porous matrix of the microsponge.

Crosslinked collagen can be prepared from both soluble collagens and insoluble collagens of the Types I, II and III. The soluble collagens are prepared by limited enzymatic digestion and/or extraction of tissue enriched in such collagen types. Insoluble collagens are derived from the following typical sources: Type I collagen: bovine, porcine, chicken and fish skin, bovine and chicken tendon and bovine and chicken bones including fetal tissues; Type II collagen: bovine articular cartilage, nasal septum, sternal cartilage; and Type III collagen: bovine and human aorta and skin. For example, Type I collagen from bovine corium and Type I tendon collage may be used.

In order to be suitable for culturing high concentrations of organisms in motive reactor systems and allow for the transfer of nutrients to the immobilized organisms and the transfer of desired products from the microsponge, the microsponge of the present invention must satisfy several functional requirements. The microsponge typically is in the shape of a bead and should have a particle size within the range of about 100 microns to 1000 microns, preferably from about 200 microns to 500 microns. At larger particle sizes the entire internal volume of the porous structure is not utilized effectively for producing the desired product by reaction between the immobilized bioactive material and the liquid medium contacted therewith, thus degrading the volumetric productivity of the motive reactor employing such microsponges. Smaller particles sizes present practical problems in preparing the microsponge and in operating the motive reactor.

Permeability of the microsponge is another important consideration. A microsponge's permeability is determined by the interrelationship of its porosity or void fraction and its pore structure. Void fraction is defined as the ratio of the volume of interstices of a material to the total volume occupied by the material and often is expressed as a percentage. In order to permit operation at high organism concentrations, the microsponge should have a void fraction of between about 70% and 98%. Preferably the void fraction of the microsponge is greater than 85% and most desirably is greater than about 90%.

The microsponge also must possess an open to the surface pore structure. This allows for cell entry, without excessive shear forces, cell retention, subsequent cell growth, and expulsion of excess cell mass. For example in cases where the desired product is not secreted by the organisms, e.g., genetically engineered *E. coli* with a nonexpressed rDNA product such as insulin, the organism must be able to escape the microsponge as the immobilized colony expands by division. An open pore structure is essential if this process is to proceed on a continuous basis, without rupturing the microsponge structure. The desired organism product is recovered as an entrained component of the culture harvest liquor.

The microsponge should contain pores with an average size within the range of about 1 micron for the smallest microbes and for viruses, up to about 100 microns for large mammalian and plant cells. Generally, the pores of the microsponge must be at least as large as the smallest major dimension of the immobilized bioreactive material but less than about 5 times the largest major dimension. Preferably, the pore size of the matrix is on the order of 1.5 to 3 times the average diameter of the organism or cell. If unknown, the smallest and largest major dimensions of an organism can be determined using known techniques. Applicants have found that the recited combination of particle sizes and pore sizes insure adequate mass transfer of constituents such as nutrients to the immobilized organisms, as well as adequate mass transfer of constituents, such as desired metabolites from the immobilized organisms.

For use in motive reactor systems, the microsponge also must be weighted. Polymeric materials suitable for use as the matrix material of the microsponge of the present invention generally have a specific gravity of about 1.0 or less. For proper operation in a motive reactor, a specific gravity of above about 1.05, preferably above about 1.3 and most preferably between about 1.6 and 2.0 is desired. It has been found surprisingly that it is possible to obtain microsponges of the proper specific gravity using the disclosed biocompatible polymeric materials by introducing certain weighting additives into the microsponge without undesirably reducing its void fraction. The weighting additive must be substantially inert in the reactor environment and non-toxic to the immobilized organism, or must be suitably treated to render the additive non-toxic. Also, the weighting additive should not adversely affect the productivity of the immobilized organism. Generally, materials, such as metals and their alloys and oxides and ceramics, preferably having a specific gravity above about 4.0 and most preferably above about 7.0 are used. Examples of suitable weighting additives for use in the broad practice of the present invention are chromium, tungsten, molybdenum, cobalt, nickel, titanium and alloys, e.g., Monel, 316 stainless Vitalium (a cobalt alloy with chromium and molybdenum), titanium 6Al-4V (a titanium alloy with 6% aluminum and 4% vanadium) and Haynes Stellite Alloy 25 (a cobalt alloy with chromium, nickel, tungsten and manganese). Many of these materials, however, may not be compatible with certain organisms and routine experimentation will be necessary to assess toxicity for any application. For example, in the case of hybridomas titanium is the weighting material of choice, since most other metals are cytotoxic.

The weighting additive can be introduced into and dispersed throughout the microscope as a finely divided powder, with most particles having a size on the order of 10 to 40 microns. However, to minimize the surface area of the weighting additive, it is desirable to employ it as a solid core in the microsponge. Sufficient weighting material is added to yield a microsponge with the desired specific gravity. For example, about a 100 micron diameter core of a weighting additive having a specific gravity of about 7.0 coated with a 50 micron thick layer of collagen having an average pore size of 20 to 40 microns and avoid fraction of about 99% yields a microsponge with a specific gravity of about 1.7 having an overall void fraction of about 85%. Such a microsponge is particularly suitable for use in an aerobic motive reactor system.

Finally, for motive applications the microsponge should exhibit the proper resistance to attrition. A charge of microsponges preferably should have a useful life on the order of three to six months or more. Typically, the microsponges should exhibit not greater than about a 10% loss in volume after three months of operation.

Normally, organisms exhibit wide variation in their degree of attachment to solid supports. Certain organisms, for example, readily cling or attach to a wide variety of supports, including both organic and inorganic materials, while others will only attach to supports of biological origin (attachment-dependent organisms). Other organisms exhibit little direct attachment to any support material (attachment-independent organisms). The microsponge of the present invention, because it is prepared from polymeric (organic) materials and because of its permeability (porosity and pore structure) should be suitable for immobilizing substantially all types of organisms.

Any suitable procedure used by the prior art for immobilizing such organisms on microsponges can be used in the present invention including such techniques as adsorption and chemical coupling. For example, in the case of certain organisms it will only be necessary to mix the microsponge in a broth inoculated with the specific organism. After a short period of time, the organism will colonize the microsponge and become entrapped in its pores. In the case of some organisms such as fibroblasts and hybridomas, it also may be desirable to coat the microsponge with attachment-promoting materials such as fibronectin, polylysine and anti-hybridoma antibodies prior to inoculation. Other techniques can also be used, such as applying a net charge to the surface of the microsponge, to enhance immobilization.

As will be recognized by those skilled in this art, in the board practice of the present invention, the procedure used for brining the immobilized bioactive material into direct contact with a reagent stream such as a growth supporting medium for culturing of immobilized organisms is not critical and any of the numerous arrangements available in the prior art including such well known apparatus as stirred tank reactors, fixed bed reactors, fluidized bed reactors and moving bed reactors and the like could be used. Generally, when culturing organisms the microsponges are charged to a suitable reactor and mixed therein with a nutrient broth and an innoculum of the organism. The microsponges should be completely submerged. The microsponges are incubated so that the organisms grow and colonize the porous matrix of the microsponge. Fresh nutrient broth along with other materials necessary for growth, such as oxygen in the case of aerobic organisms, are supplied in a continuous manner to the reactor and harvest liquor containing the biocohemical product of interest is recovered. The biocohemical product may comprise a primary or secondary metabolite of an immobilized organism, excess biomass generated by an immobilized organism containing for example a non-secretory product, an immobilized enzyme catalyzed reaction product or the like.

A particular advantage of the microsponges of the present invention is that they can be used in a mixed or motive system such as a fluidized bed reactor. As used herein, the term "motive reactor" refers to reactor systems in which relative motion between the microsponge and the fluid medium is provided in part by imparting motion to the microsponge themselves. Such reactor systems substantially enhance mass and energy transfer.

To prepare a microsponge of crosslinked collagen material, a collagen source is formed into a collagen-based solution or dispersion by admixture with a suitable solvent such as an acid using, for example, a Waring blender. Next, the weighting additive is blended with the collagen-liquid mixture and the composite mixture is solidified into dry beads using known drying techniques such as spray drying, freeze-drying and the like. Any known technique for producing small beads can be employed in carrying out the present invention. Suitable techniques include, inter alia, pressure or air-shear spraying, emulsification techniques, droplet formation using Raleigh liquid jet instability techniques, extrusion techniques, droplet formation using gravity or centrifugal forces, electrostatic droplet formation, and droplet formation using inertial forces. For example, suitably sized particles have been prepared using inertial forces to form small droplets at the orifice of a vibrating needle. Also, larger sized particles possibly could be reduced to the desired particle size by such destructive techniques as grinding and the like. Still additional techniques such as various coating methodologies, could be used to form microsponges having a solid core of the weighting additive. In this case a shell of the collagen matrix would surround the weighted core. Those skilled in the art will recognize other techniques suitable for forming small particles of the types described above and the present invention is not intended to be limited to any specific technique. Finally, the collagen is crosslinked using a suitable treatment as noted above.

Preferably, the microsponges are then sterilized using conventional sterilization techniques and are aseptically packaged for delivery to the ultimate consumer. The microsponges preferably are sterilized using gamma irradiation. Ethylene oxide also may be used as an alternative, as may additional sterilization procedures known to those skilled in the art, as long as the important characteristics of the microsponge are not compromised. Obviously, when sterilizing the microsponges using ethylene oxide the particles must be thoroughly ventilated in order to remove all traces of this sterilizing agent before subsequently using the microsponges for culturing organisms. To use the sterilized microsponges, the user simply places the microsponges into a previously sterilized reactor, adds the proper nutrients and innoculum and initiates operation. In a preferred embodiment, the package actually comprises a disposable reactor vessel having the necessary connections for feeding a nutrient stream, for removing a harvest liquor and for ancillary operations, as needed, such as heat exchange, oxygenation and process control. For a fluidized bed reactor, the vessel also would contain a suitably designed distribution plate. Such a pre-packaged disposable reactor vessel may have a volume between about 0.1 liter and 10 liters. In this case, the user of the reactor simply integrates it with the other process equipment consisting of pumps, valves, piping heat and gas exchangers and various instrumentation and related probes and begins operation. Providing a disposable reactor, pre-packaged with the microsponges sterilized and ready for use, significantly simplifies start-up procedures for culturing organisms, particularly when changing from one culture to another.

Figure 2:
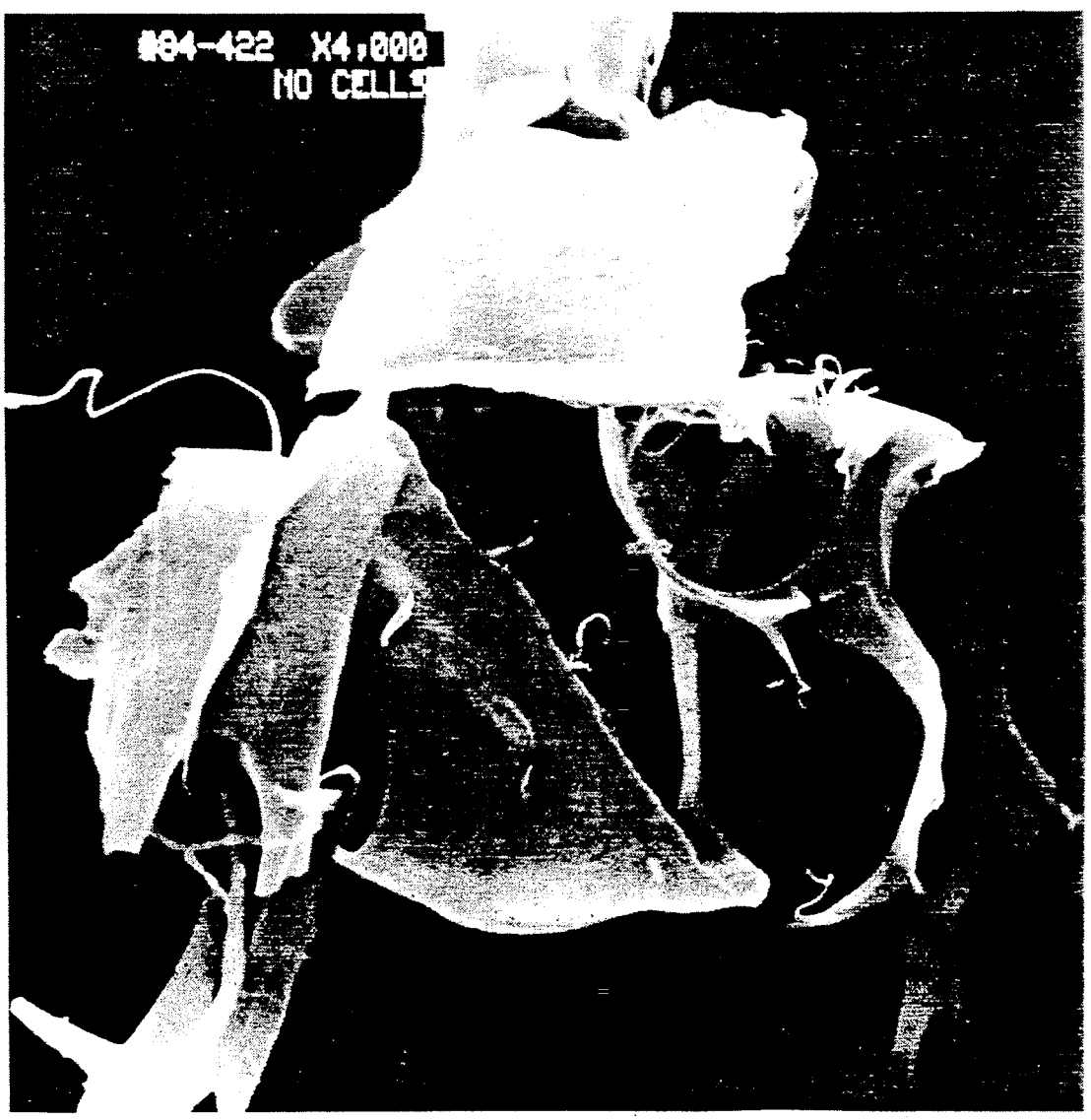
FIG. 2 is a photomicrograph of another collagen microsponge matrix according to the present invention illustrating a leafy structure.

FIG. 1 illustrates a collagen matrix having substantially a wire-mesh structure. In this structure, the diameter of the fiber network typically is on the order of about 1 micron. FIG. 2 illustrates a leaf-type matrix structure. The leaves of this structure typically have a thickness on the order of about 1 micron.

The following example is intended to more fully illustrate the invention without acting as a limitation on its scope.

EXAMPLE 1

This example describes a suitable method for preparing weighted microsponges of crosslinked collagen. Weighted microsponges prepared by this procedure can have particle sizes within the range of about 200 to 800 microns, void fractions of about 80%, pore sizes on the order of about 20 to 40 microns, and specific gravities on the order of about 1.1. The microsponges can be used to support the growth of hybridoma cells.

Partially purified tendon collagen is milled to obtain small fibers, for example using a Wiley Mill available from VWR Scientific. The collagen is dispersed into an acidic solution using a Waring blender so as to produce a collagen dispersion having about 1.0% (by weight) collage. An inert weighting additive, e.g., titanium, then is added to the collage dispersion as a fine powder. Frozen droplets of the composite mixture can be formed by flowing the mixture through a vibrating hollow needle which discharges into a cryogenic bath of liquid nitrogen. The frozen droplets are then vacuum dried, for example using a Virtis Freezemobile Lyophilizer Model 6. After lyophilizaiton, the collagen in the dried microsponges can be crosslinked by severe dehydration (dehydrothermal treatment) at a temperature of about 100° C. under a vacuum of about 10 millitorr for about 72 hours using a drying oven available from VWR Scientific.

About 300 ml of the microsponges can be contained in a 600 ml reactor vessel. The microsponges can be inoculated with the hybridoma cells and cultured using a suitable nutrient medium. The rector can be operated at a solids concentration of about 25%–40%, as the content of the reactor is vigorously agitated. A nutrient medium such as Delbecko Modified Eagle medium with 10% fetal calf serum can be passed into the reactor in a continuous manner and a product stream containing the monoclonal antibodies can be recovered at a substantially equivalent flow rate.

It will be obvious to one of ordinary skill that numerous modifications may be made without departing from the true spirit and scope of the invention which is to be limited only by the appended claims.

We claim:

1. A weighted microsponge for immobilizing bioactive materials in motive bioreactor systems, said microsponge comprising a porous, biostable matrix of a biocompatible polymer containing an inert weighting material, said matrix having an open to the surface pore structure with an average pore size in the range of from about 1 to about 150 microns, the pores of said matrix occupying from about 70% to about 98% by volume of the microsponge, said microsponge also having an average particle size of from about 100 to about 1000 microns and a specific gravity of above about 1.05.

2. The microsponge of claim 1 having immobilized therein bioactive materials selected from the group consisting of enzymes, microorganisms, dead cells and living cells.

3. The microsponge of claim 1 wherein said biostable, biocompatible polymer is selected from the group consisting of cellulose, dextran, dextrin, polyamides, polyesters, starch, agarose, carrageenan, polyurethanes, polyvinyl alcohols, polyacrylates, polymethacyrlates and polyacrylamides.

4. The microsponge of claim 1 wherein said inert weighting material is selected from the group consisting of metals, metal alloys, metal oxides and ceramics.

5. The microsponge of claim 4 wherein said weighting material has a specific gravity of above about 4.0 and said microsponge has a specific gravity of above about 1.3.

6. The microsponge of claim 5 wherein said inert weighting material is dispersed throughout said porous matrix as finely divided powder.

7. The microsponge of claim 5 wherein said weighting material is centrally disposed as a solid core about which said porous matrix is formed.

8. The microsponge of claim 5 wherein said inert weighting material is selected from the group consisting of chromium, tungsten, cobalt, molybdenum, titanium, nickel and alloys.

9. The microsponge of claim 8 wherein said weighting material is titanium and said microsponge has hybridoma cells immobilized therein.

10. The microsponge of claim 6 wherein said porous matrix is a collagen matrix.

11. A bioreactor system comprising a reactor vessel having aseptically sealed therein a plurality of sterilized weighted microsponges for immobilizing bioactive materials in motive bioreactor systems, said microsponges comprising a porous, biostable matrix of a biocompatible polymer containing an inert weighting material, said matrix having an open to the surface pore structure with an average pore size in the range of from above about 1 to about 150 microns, the pores of said matrix occupying from about 70% to about 98% by volume of the microsponge, said microsponge also having an average particle size of from bout 100 to about 1000 microns and a specific gravity of above about 1.05.

12. The bioreactor system of claim 11 wherein said reactor has a volume between about 0.1 to 10 liters.

13. The bioreactor system of claim 12 wherein said reactor is a fluidized bed reaction, having a fluid distribution plate.

14. A process for performing a bioreaction comprising: immobilizing a bioactive material in weighted microsponges comprising a porous, biostable matrix of a biocompatible polymer containing an inert weighting material, said matrix having an open to the surface pore structure with an average pore size in the range of from about 1 to about 150 microns, the pores of said matrix occupying from about 70% to about 98% by volume of the microsponge, said microsponge also having an average particle size of from about 100 to about 1000 microns and a specific gravity of above about 1.05, retaining the microsponges having said immobilized bioactive materials in a suitable reactor vessel; passing a liquid reagent stream into said reactor in direct contact with said microsponges; agitating the mixture of said microsponges and said reagent stream and recovering the biocohemical reaction products from said reactor.

15. The process of claim 14 wherein organisms are immobilized in said microsponges, the microsponges are incubated to promote growth and colonization of said microsponges by said organisms, said reagent comprises nutrient media for promoting the growth and metabolism of said organisms, and wherein said product comprises metabolites of said organisms.

16. The process of claim 14 wherein organisms are immobilized in said microsponges and the recovered product comprises free organisms which have escaped from said microsponges.

17. The process of claim 15 wherein organisms comprises hybridomas and said product comprises monoclonal antibodies.

18. The process of claim 17 wherein said reactor vessel comprises a fluidized bed reactor.

19. The process of claim 15 wherein said organisms comprise mammalian cells and said products comprise mammalian cell products.

20. The process of claim 15 wherein said organisms are genetically engineered microbial organisms and said product comprises secreted protein products.

21. The process of claim 16 wherein organisms are genetically engineered microbial cells and said product comprises said cells containing a non-secreted protein product.

* * * * *